(12) United States Patent
Fritz

(10) Patent No.: US 7,262,838 B2
(45) Date of Patent: *Aug. 28, 2007

(54) OPTICAL DETECTION SYSTEM FOR FLOW CYTOMETRY

(75) Inventor: Bernard S. Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 425 days.

This patent is subject to a terminal disclaimer.

(21) Appl. No.: 10/759,875

(22) Filed: Jan. 16, 2004

(65) Prior Publication Data

US 2004/0145725 A1  Jul. 29, 2004

Related U.S. Application Data

(63) Continuation-in-part of application No. 09/896,230, filed on Jun. 29, 2001, now Pat. No. 6,700,130, and a continuation-in-part of application No. 10/304,773, filed on Nov. 26, 2002.

(51) Int. Cl.
*G01N 21/00* (2006.01)
(52) U.S. Cl. .......................... 356/73; 356/335
(58) Field of Classification Search .............. None
See application file for complete search history.

(56) References Cited

U.S. PATENT DOCUMENTS

| 3,822,095 | A | 7/1974 | Hirschfeld |
|---|---|---|---|
| 3,976,862 | A | 8/1976 | Curbelo |
| 4,478,076 | A | 10/1984 | Bohrer |
| 4,478,077 | A | 10/1984 | Boher |
| 4,501,144 | A | 2/1985 | Higashi et al. |
| 4,651,564 | A | 3/1987 | Johnson et al. |
| 4,683,159 | A | 7/1987 | Bohrer et al. |
| 4,695,034 | A | 9/1987 | Shimizu et al. |
| 4,745,279 | A | 5/1988 | Karkar et al. |

(Continued)

FOREIGN PATENT DOCUMENTS

EP            1001326            5/1999

(Continued)

OTHER PUBLICATIONS http://www.micronics.net/tsensor.htm, pp. 1-4, downloaded Jun. 14, 2000.

(Continued)

*Primary Examiner*—Roy M. Punnoose
(74) *Attorney, Agent, or Firm*—Kris T. Fredrick

(57) ABSTRACT

An optical detection system for flow cytometry that uses two or more light sources positioned laterally at different distances from a central axis of a flow stream for providing light through different parts of the flow stream. One or more lenses are used to focus the light from the two or more light sources through the flow stream and onto a common focal point or region on the opposite side of the flow stream. One or more light detectors are then placed at, near or around the common focal point or region. A processor or the like receives at least one output signal from the one or more light detectors to analyze and determine selected characteristics of the flow stream.

12 Claims, 14 Drawing Sheets

U.S. PATENT DOCUMENTS

| | | | |
|---|---|---|---|
| 4,874,949 A | 10/1989 | Harris et al. | |
| 4,911,616 A | 3/1990 | Laumann, Jr. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez | |
| 5,633,724 A | 5/1997 | King et al. | |
| 5,683,159 A | 11/1997 | Johnson | |
| 5,716,852 A | 2/1998 | Yager et al. | |
| 5,726,751 A | 3/1998 | Altendorf et al. | |
| 5,757,476 A | 5/1998 | Nakamoto et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,082,185 A | 7/2000 | Saaski | |
| 6,097,485 A | 8/2000 | Lievan | |
| 6,106,245 A | 8/2000 | Cabuz | |
| 6,109,889 A | 8/2000 | Zengerle et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,549,275 B1 * | 4/2003 | Cabuz et al. | 356/39 |
| 6,597,438 B1 * | 7/2003 | Cabuz et al. | 356/39 |
| 6,700,130 B2 * | 3/2004 | Fritz | 250/573 |

FOREIGN PATENT DOCUMENTS

| | | |
|---|---|---|
| WO | WO95/27199 | 3/1995 |
| WO | WO99/60397 | 4/1999 |
| WO | WO01/09598 | 7/2000 |

OTHER PUBLICATIONS http://www.micronics.net/hfilter.htm, pp. 1-3, downloaded Jun. 14, 2000.
http://www.micronics.net/mcytometry.htm, pp. 1-4, downloaded Jun. 14, 2000.
http://www.micronics.net/orcafluidics.htm, pp. 1-4, downloaded Jun. 14, 2000.
Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.
Altendorf et al., "Differential Blood Cell Counts Obtained Using A Microchannel Based Flow Cytometer", Solid State Sensors & Actuators, vol. 1, 531, 1997.
Altendorf et al., "Microfabrication Technology For Research And Diagnostics, Silicon Microchannel Optical Flow Cytometry", SPIE Proceedings, Biomedical Optics 96, Jan. 1996.
Altendorf et al., "Results Obtained Using A Prototype Microfluidics-Based Hematology Analyzer", SPIE Biomedical Optics 97, 1997.
Cabuz et al., "Mesoscopic Sampler Based on 3D Array of Electrostatically Activated Diaphragms", Transducers '99, The 10th International Conference on Solid-State Sensors and Actuators, Digest of Technical Papers, vol. 2, Jun. 7-10, 1999.
Darling et al., "Integration Of Microelectrodes With Etched Microchannels For In-Stream Electrochemical Analysis", MicroTAS 98, Banff, Canada, Apr. 1998.
Hatch et al., "Microfluidic Approaches To Immunoassays", SPIE conference on Micromachining and Microfabrication Symposium at Santa Clara, CA, Sep. 20-22, 1999.
Huang, et al., "Development Of A Flow Cytometry Based Miniature Chemical Fluid Analysis System Using Fluorescent Microbeads", SPIE Biomedical Optics, BIOS 97, conference proceedings, 1997.
Lehman et al., "High-Frequency Modulation Characteristics of Red VCSELs", Electronics Letters, Feb. 13, 1997, vol. 33(4), pp. 298-300. Copyright 1997 IEE.
Ohnstein et al., "Micromachined Silicon Microvalve", Proceedings of MEMS, 1990, IEEE Micro Electrochemical Systems, Napa Valley, California, Feb. 11-14, 1990, pp. 95-98.
Roulet et al., "Fabrication of Multilayer Systems Combining Microfluidic and Microoptical Elements for Fluorescence Detection," Journal of Microelectromechanical Systems, vol. 10, No. 4, pp. 482-491, Dec. 2001.
Shapiro, "Practical Flow Cytometry", third edition, 1995, p. 237.
Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.
Terstappen, et al., "Four-Parameter White Blood Cell Differential Counting Based on Light Scattering Measurements", Alan R. Liss, Inc., Cytometry 9:39-43, 1988.
Weigl et al., "Silicon-microfabricated diffusion-based optical chemical sensor," Sensors and Actuators, B 38-39, pp. 452-457, 1997.
Weigl et al., "Diffusion-Based Optical Chemical Detection In Silicon Flow Structures", Analytical Methods & Instrumentation, μTTAS 96 special edition, 1996.
Weigl et al., "Microfluidic Diffusion-Based Separation And Detection", Science, vol. 283, pp. 346-347, Jan. 15, 1999.
Weigl et al., "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.
Weigl et al., "Rapid Sequential Chemical Analysis Using Multiple Fluorescent Reporter Beads", μTTAS 96 Conference Proceedings, 1996.
Weigl et al., "Simultaneous Self-Referenceing Analyte Determination In Complex Sample Solutions Using Microfabricated Flow Structures (T-Sensors™)", Proceedings of MicroTAS 98, 81-4, Banff, Canada, 1998.
Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Outline, http://news.medicaldesignonline.com/featuresarticles/19990416-5922.html, Apr. 1999.

Weigl, et al., "Fluorescence and Absorbance Analyte Sensing In Whole Blood Based On Diffusion Separation In Silicon-Microfabricated Flow Structures," SPIE Proceedings, J. Lakowitz (ed.), Advances in Fluorescence Sensing Technology III, 1997, pp. 171-181.

Yager et al., "Design Of Microfluidic Sample Preconditioning Systems For Detection Of Biological Agents In Environmental Samples", SPIE Proceedings, 3515, 252-259, 1998.

Yager et al., "Applying Microfluidic Chemical Analytical Systems To Imperfect Samples", Micro Total Analysis Systems 98, Kluwer Academic Publishers, Dordrecht, 207-212, 1998.

* cited by examiner

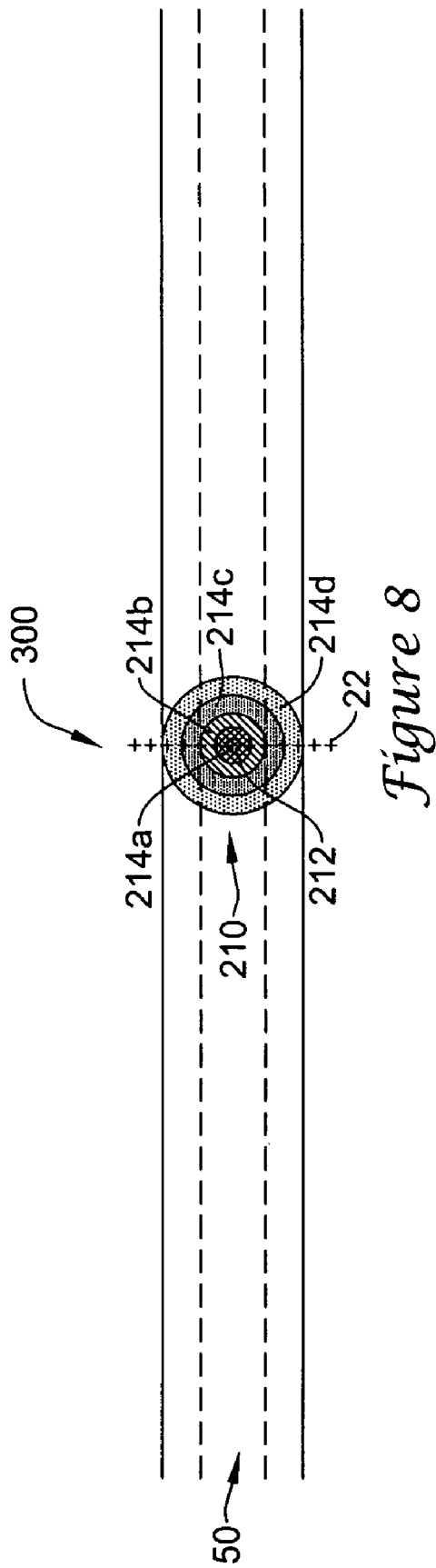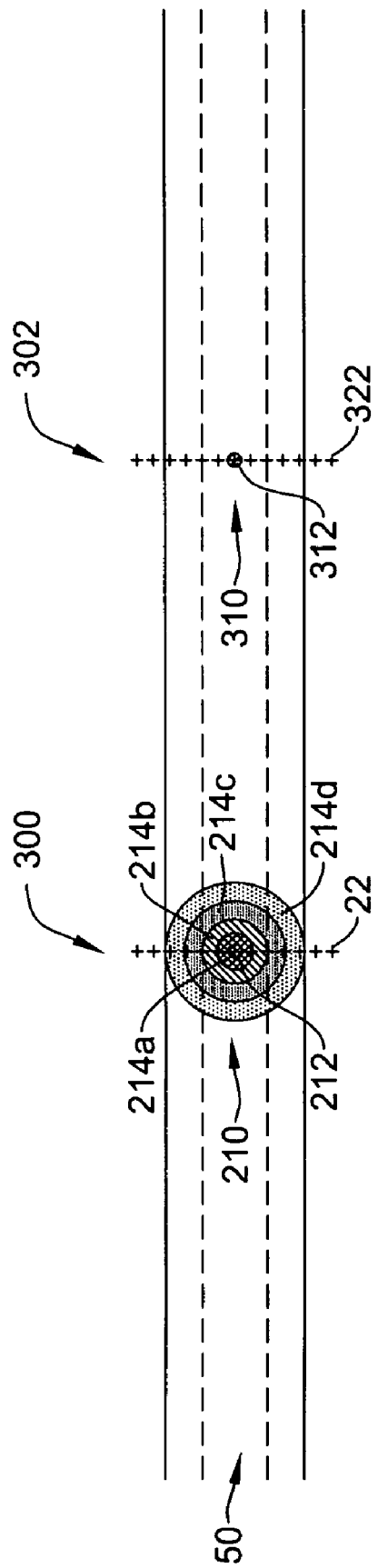

OPTICAL DETECTION SYSTEM FOR FLOW CYTOMETRY

The present patent application claims priority as a continuation-in-part of U.S. Nonprovisional patent application Ser. No. 09/896,230, filed Jun. 29, 2001 now U.S. Pat. No. 6,700,130, U.S. Patent Application Publication No. US 2003/0002027 A1, published Jan. 2, 2003, and entitled "Optical Detection System for Flow Cytometry", which is hereby incorporated by reference in its entirety in the present application. The present patent application claims priority as a continuation-in-part of U.S. Nonprovisional patent application Ser. No. 10/304,773, filed Nov. 26, 2002, U.S. Patent Application Publication No. US 2003/0142291 A1, published Jul. 31, 2003, and entitled "Portable Scattering and Fluorescence Cytometer", which is hereby incorporated by reference in its entirety in the present application.

This Application is related to co-pending U.S. patent application Ser. No. 09/630,927 to Cabuz et al., filed Aug. 2, 2000, and entitled "OPTICAL DETECTION SYSTEM FOR FLOW CYTOMETRY", which is incorporated herein by reference.

BACKGROUND

The present invention relates generally to flow cytometers. More particularly, the present invention relates to optical detection systems for flow cytometer systems.

Flow cytometry is a technique that is used to determine certain physical and chemical properties of microscopic biological particles by sensing certain optical properties of the particles. Flow cytometry is currently used in a wide variety of applications including hematology, immunology, genetics, food science, pharmacology, microbiology, parasitology and oncology.

In flow cytometry, the microscopic biological particles of a sample fluid are arranged in single file in a core stream, typically using hydrodynamic focusing. The particles are then individually interrogated by an optical detection system. The optical detection system provides a light beam, which is scattered by each particle to produce a scatter profile. The scatter profile is analyzed by measuring the light intensity at both small and larger scatter angles. Certain physical and/or chemical properties of each particle can then be determined from the scatter profile.

Conventional cytometer systems use a single light source such as a laser to interrogate each particle. The light beam is often focused to an elongated shape that covers the uncertainty in particle position due to misalignment and variations in the width of the core stream. A limitation of using a single light source is that the particle position and variations in the width of the core stream cannot be directly detected. Misalignments in particle position and variations in the width of the core stream can be indicators of improper core formation. Because there may be no direct way of monitoring the characteristics of the core stream, improper core formation may go undetected.

This limitation may be further compounded because the single laser source configuration often does not provide a constant illumination intensity across the flow channel. As such, particles that pass more toward the edge of the core stream may not be as illuminated as particles that pass near the center. As a result, the sensitivity and accuracy of the system may vary depending on the lateral position of the particle through the focused elongated shape beam. Since there may be no easy way of detecting the lateral position of each particle, the variations in sensitivity and accuracy may go undetected.

Another limitation of using a single light source is that the velocity of each particle cannot be directly determined. Particle velocity is often an important parameter in estimating the particle size from light scatter signals. In conventional flow cytometry systems, the velocity of each particle is extrapolated from the pump flow rates. Accordingly, to accurately gauge the velocity of each particle, the pumps must be very precise, the tolerance of the cytometer flow chambers must be tightly controlled, no fluid failures such as leaks can occur, and no obstructions such as microbubbles can be introduced to disturb the flow or core formation. Satisfying these constraints can add significant complexity and cost to the flow cytometer system.

SUMMARY

The present invention overcomes many of the disadvantages of the prior art by providing an optical detection system that uses two or more light sources positioned laterally at different distances from a central axis of a flow stream for providing light through different parts of the flow stream. One or more lenses are used to focus the light from the two or more light sources through the flow stream and onto a common focal point or region on the opposite side of the flow stream. One or more light detectors are then placed at, near or around the common focal point or region. A processor or the like may then receive at least one output signal from the one or more light detectors to analyze and determine selected characteristics of the flow stream.

In one illustrative embodiment of the present invention, an array of light sources and an array of lenses are used to illuminate a flow stream. To focus the light from each of the light sources through the flow stream to a common focal point or region on the opposite side of the flow stream, the pitch of the lens array is slightly different than the pitch of the light source array. This creates an offset between the optical axis of each lens and the corresponding light source, and this offset varies across the arrays. The various offsets are preferably set so that each lens focuses the light from the corresponding light source onto the common focal point or region on the opposite side of the flow stream. A multiple annular zoned detector is then positioned at, near or around the common focal point or region to measure the incident intensity distribution over various angular zone regions.

Blood cells or other particles present in the flow channel tend to diffract or scatter the light out of the central zone of the annular zoned detector and onto outer annular detector zones. Analysis of the signal strength produced by the various annular zones can be used to determine certain physical and/or chemical properties of each particle passing through the flow channel. Such an analysis can be used to determine, for example, if a particle is present in the flow stream, the speed and alignment of the particle within the flow stream, and in many cases, the type of particle.

In one illustrative application, the optical detection system of the present invention may be used in conjunction with a portable cytometer system for detecting, for example, neutrophils and/or lymphocytes white blood cells in a blood sample. By examining the scatter distribution of each of the particles, the portable cytometer may identify and count the neutrophils and lymphocytes in the blood sample, and provide a clear infection warning with differentiation between viral and bacterial causes. Many other applications are also contemplated.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 8 is a schematic diagram showing an array of light sources positioned along an axis that is angularly offset by about ninety degrees relative to the central axis of a flow channel and a single annular zoned detector positioned on the opposite side of the flow stream;

FIG. 9 is a schematic diagram showing two arrays of light sources, each positioned along an axis that is angularly offset by about ninety degrees relative to the central axis of a flow channel, and two annular zoned detectors positioned on the opposite side of the flow stream;

DESCRIPTION

Figure 1:
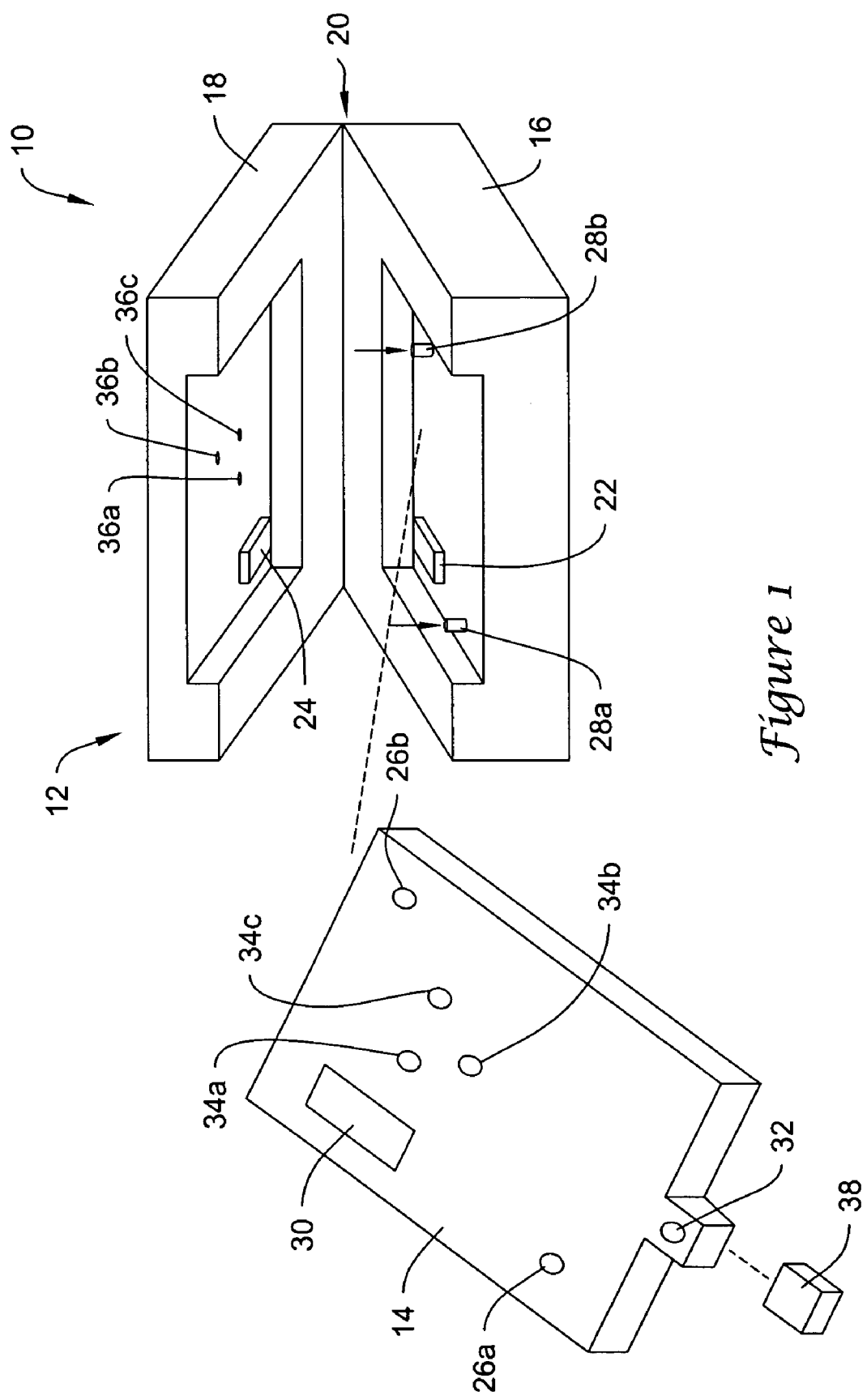
FIG. 1 is a perspective view of an illustrative portable cytometer in accordance with the present invention.

FIG. 1 is a perspective view of an illustrative portable cytometer in accordance with the present invention. The portable cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24.

The removable cartridge 14 preferably receives a sample fluid via a sample collector port 32. A cap 38 may be used to protect the sample collector port 32 when the removable cartridge 14 is not in use. The removable cartridge 14 preferably performs blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes a transparent flow stream window 30, which is in alignment with the array of the light sources 22 and light detectors 24. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform differentiation and counting of white blood cells based on light scattering signals. Rather than using a hinged construction for the housing 12, it is contemplated that a sliding cartridge slot or any other suitable construction may be used.

Figure 2:
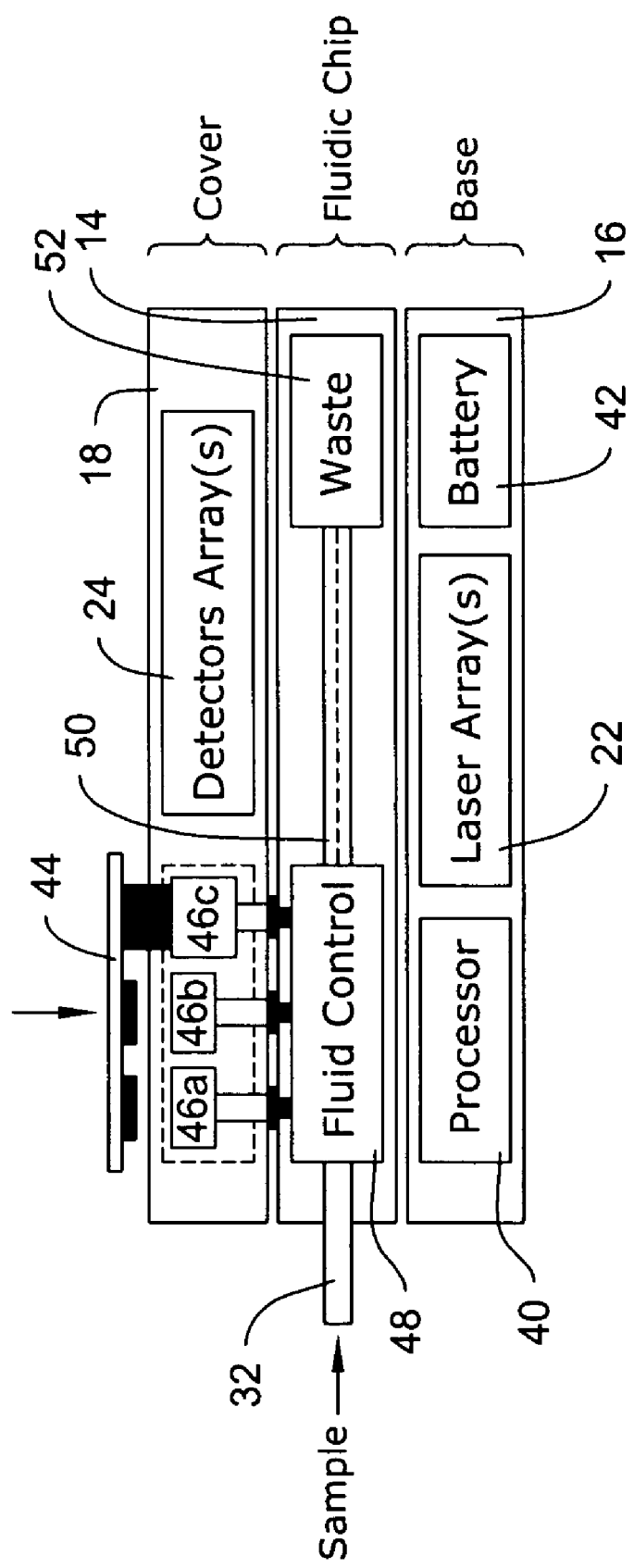
FIG. 2 is a schematic view of the illustrative portable cytometer of FIG. 1.

FIG. 2 is a schematic view of the illustrative portable cytometer of FIG. 1. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and an array of light detectors 24.

The removable cartridge 14 may receive a sample fluid via the sample collector port 32. When pressurized by the cover 18, the removable cartridge 14 performs blood dilution, red cell lysing, and hydrodynamic focusing for core formation in a preferred embodiment. Once formed, the core is provided down a flow stream path 50, which passes the flow stream window 30 of FIG. 1. The array of light sources 22 and associated optics in the base provide light through the core stream via the flow stream window 30. The array of light detectors receive scattered and non-scattered light from the core, also via the flow stream window 30. The controller or processor 40 receives output signals from the array of detectors, and differentiates and counts selected white blood cells that are present in the core stream.

Figure 3:
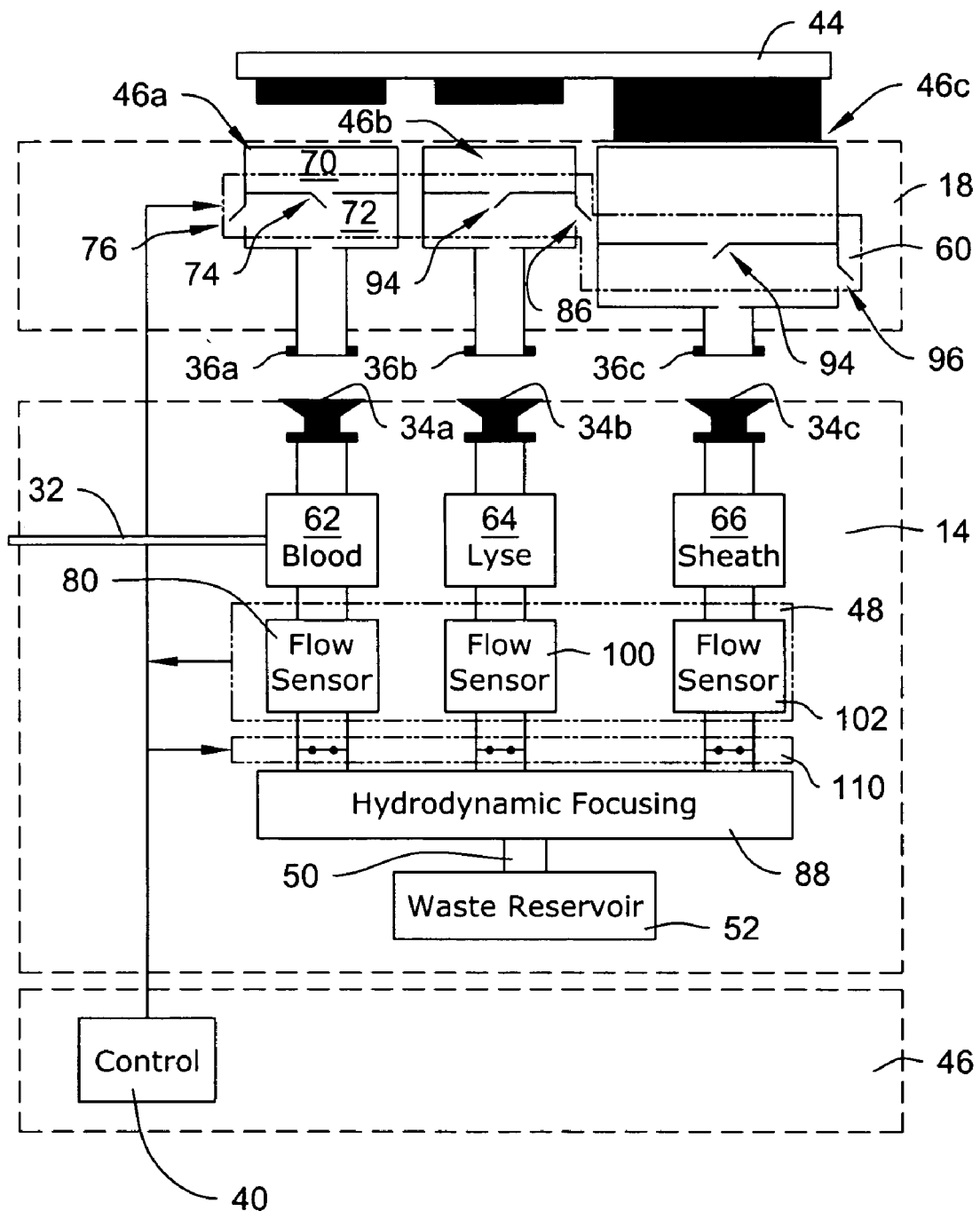
FIG. 3 is a more detailed schematic diagram showing the portable cytometer of FIG. 2 with the cover not yet depressed.
Figure 4:
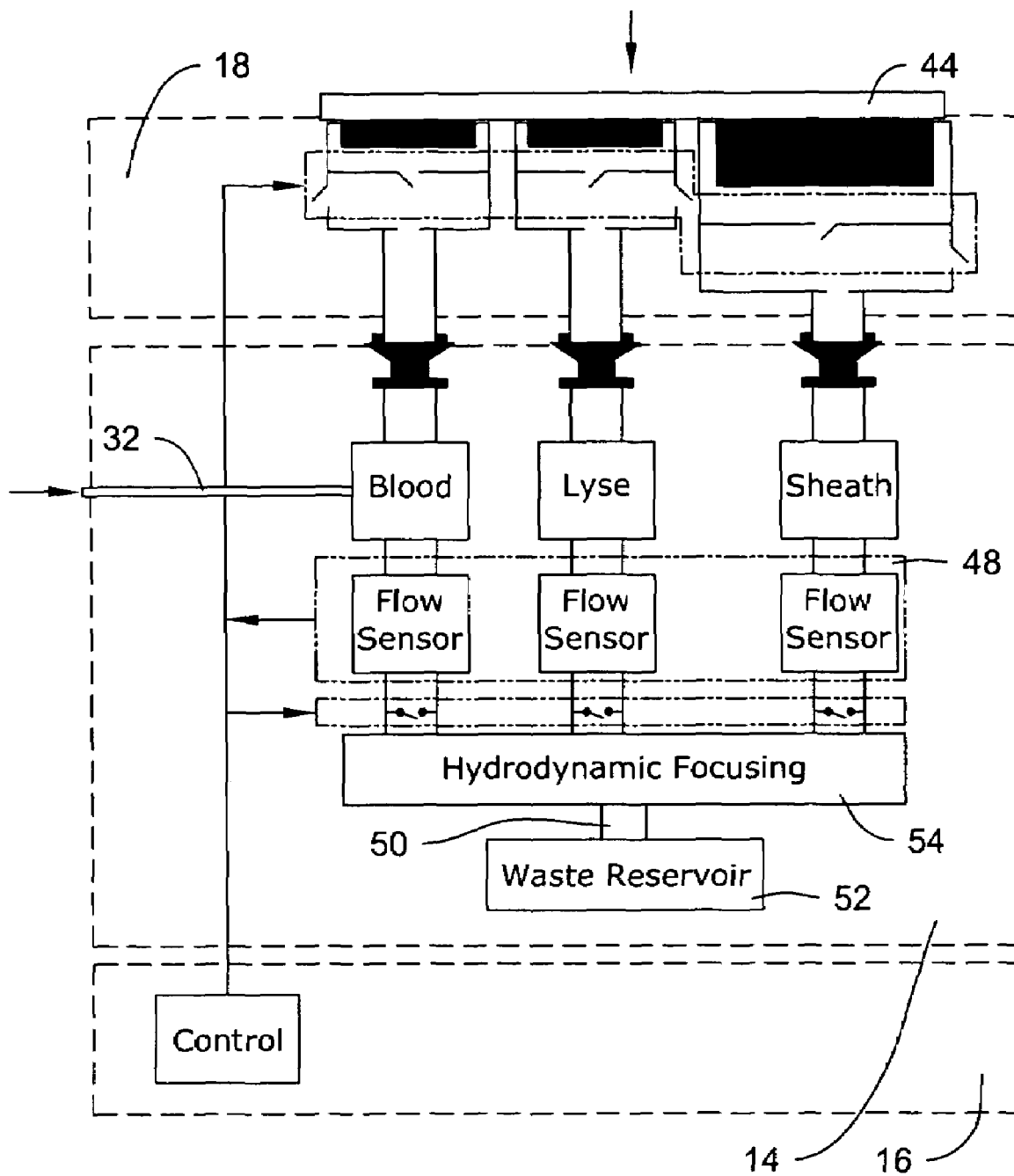
FIG. 4 is a more detailed schematic diagram showing the portable cytometer of FIG. 2 with the cover depressed.

FIG. 3 is a more detailed schematic diagram showing the portable cytometer of FIG. 2 with the cover 18 not yet depressed. FIG. 4 is a more detailed schematic diagram showing the portable cytometer of FIG. 2 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative embodiment, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors are preferably thermal anemometer type flow sensors, and more preferably microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another embodiment, downstream valves 110 are opened by mechanical action when the cover is closed.

Figure 5:
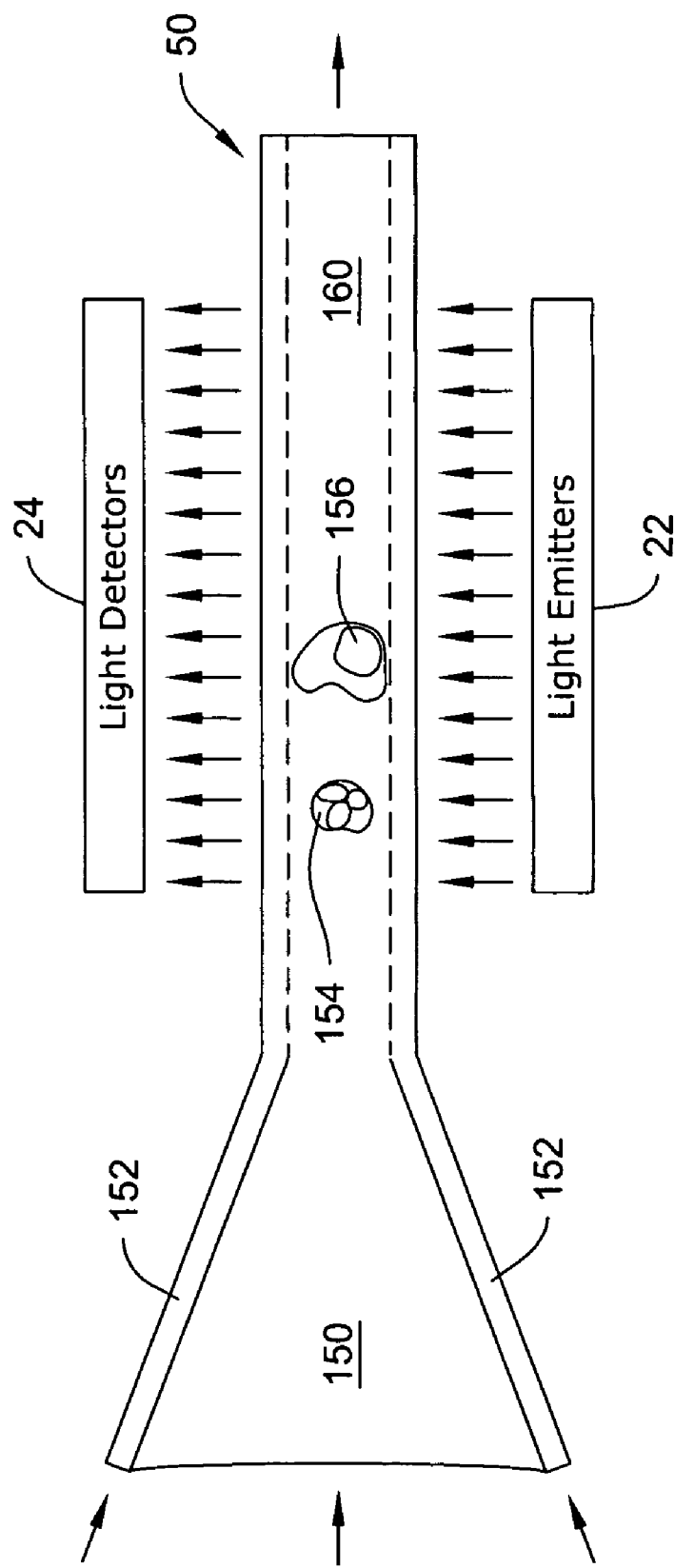
FIG. 5 is a schematic diagram showing the formation of a flow stream by the hydrodynamic focusing block 88 of FIG. 3.

FIG. 5 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. This is often referred to as red cell lysing. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the blood cells 154 and 156 are in single file. The velocity of the sheath fluid is preferably about 9 times that of the core stream 160. However, the velocity of the sheath fluid and core stream 160 preferably remain sufficiently low to maintain laminar flow in the flow channel.

Light emitters 22 and associated optics are preferably provided adjacent one side of the flow stream 50. Light detectors 24 are provided on another side of the flow stream 50 for receiving the light from the light emitters 22 via the flow stream 50. The output signals from the light detectors 24 are provided to controller or processor 40, wherein they are analyzed to identify and/or count selected white blood cells in the core stream 160. In a preferred embodiment, the blood cells 154 and 156 are white blood cells. In other preferred embodiments, the blood cells may include neutrophils and/or lymphocytes.

Figure 6:
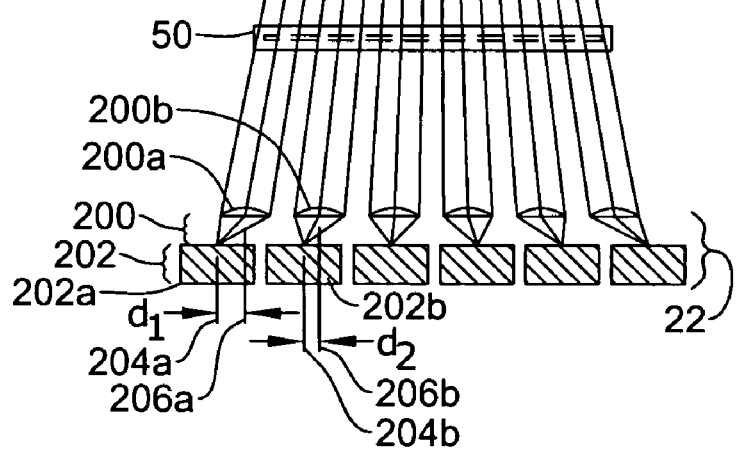
FIG. 6 is a schematic diagram showing an array of light sources, an array of lenses and a cross sectional view of an annular zoned detector.

FIG. 6 is a diagram showing an illustrative embodiment of the present invention. A lens array 200 is positioned between a light source array 202 and flow channel 50. Each lens in the lens array 200 may be a microlens. The microlenses may be any type of lens including, for example, refractive lenses, diffractive lenses, etc. An annular detector 210, with a center zone 212 and outer zones 214a, 214b, 214c and 214d, is positioned on the opposite side of the flow channel 50 from the light source array 202. A first lens 200a is positioned relative a first light source 202a such that the central focal axis 206a of the lens 200a is offset by a distance "$d_1$" from the light source central axis 204a. A second lens 200b is positioned relative a second light source 202b such that the central focal axis 206b of the lens 200b is offset by a distance "$d_2$" from the light source central axis 204b. The offset distances between the central focal axis of each lens and the corresponding light source central axis preferably changes across the array such that the light rays emitted by each light source is focused onto a common point or region 222 on the annular detector 210. As shown in FIG. 6, the common focal point 222 may appear on the annular detector 210 at or about the center of the central zone 212.

Because the lens array 200 and the light source array 202 are adapted to focus the light rays onto a common point or region 222, no beam shaping optics may be required on the detector side. This may reduce the complexity and cost of the device. Furthermore, particles that pass through the flow channel 50 may produce a simple rotationally symmetric scattering signature, which can be much easier to process at the detector than non-rotationally symmetric scattering signatures.

The light source array 202 is preferably an array of lasers such as Vertical Cavity Surface Emitting Lasers (VCSEL) fabricated on a common substrate. Because of their vertical emission, VCSELs are ideally suited for packaging in compact instruments such as a portable cytometer. Preferably, the VCSELs are "red" VCSELs that operate at wavelengths that are less than the conventional 850 nm, and more preferably in the 670 nm to 780 nm range. Red VCSELs may have a wavelength, power and polarization characteristic that is ideally suited for scatter measurements. Other light sources may be used including, for example, Light Emitting Diodes (LEDs) or any other type of light source.

Figure 7:
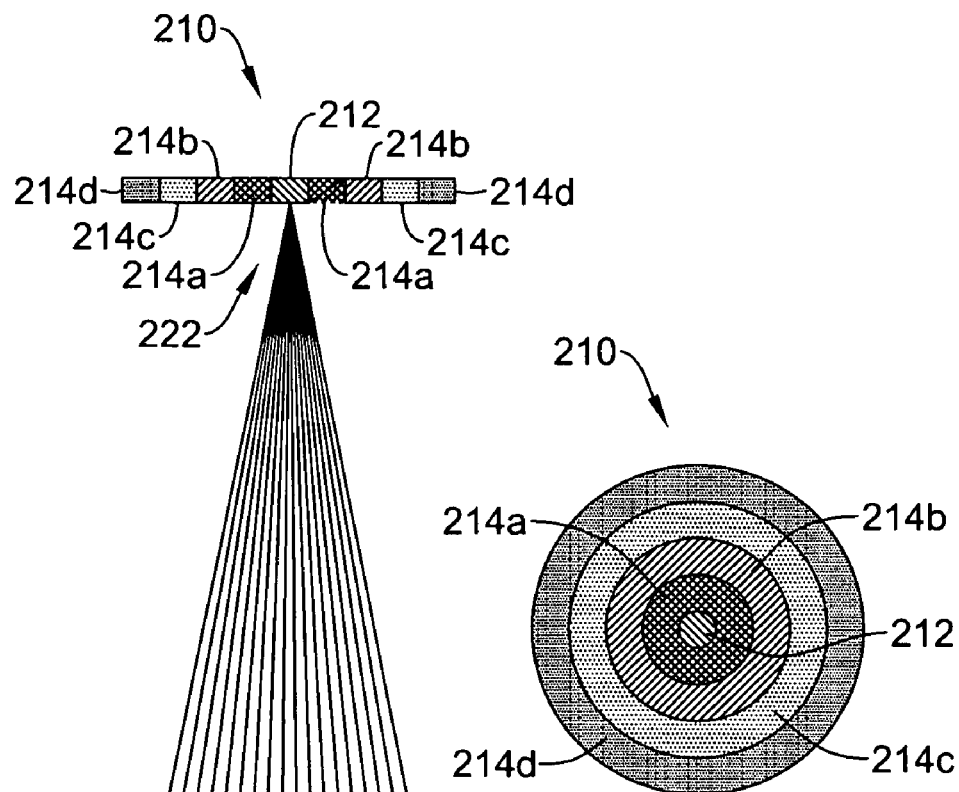
FIG. 7 is an illustrative diagram of a top frontal view of the annular zoned detector of FIG. 6.

FIG. 7 is a frontal view of the annular detector 210 shown in FIG. 6. The illustrative annular detector has several zones, including a central zone 212 and several annular shaped outer zones 214a–d. The first zone 214a, which is located just outside of the central zone 212, may be an annular shaped light detector used for detecting forward angle scattering (FALS) produced by one or more particles in the flow stream. The second zone 214b, which is positioned outside of the first zone 214a, may be an annular shaped light detector used for detecting the small angle scattering (SALS) produced by one or more particles in the flow stream. Other annular shaped light detectors 214c and 214d may be positioned outside of the central detector 212 and the first two annular shaped outer detectors 214a and 214b to detect other scatter angles, as desired.

FIG. 8 is a schematic diagram showing a linear array of light sources 22 (indicated by "+" signs) positioned along an axis that is angularly offset by about ninety degrees relative to the central axis of flow of a flow channel 50. FIG. 8 also shows a single annular shaped zoned detector 210 positioned on the opposite side of the flow channel 50. In a preferred embodiment, the light sources 22 are designed with lenses as shown in FIG. 6 so that the light emitted from the array of light sources 22 will have a common focal point or region on the central ring 212 of the detector 210. Preferably, the array of light sources 22 are positioned and spaced to provide a substantially constant light intensity across the width of the flow channel 50.

Using a linear array of lasers offers a number of important advantages over the single light source configuration. For example, a linear array of lasers may be used to determine the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 (see FIG. 2) to adjust the valves of the fluid driver in order to change the relative pressures that are applied to the sample fluid and the supporting fluids to change the alignment of the selected particles in the flow stream.

To determine the lateral alignment of the particles in the fluid stream 50, the particles pass through the light produced by the linear array of VCSELs. The particles produce a different scatter profile at the detector when the cells are not properly aligned. The relative strengths of the signals at the detector 210 can be used by the controller or processor 40 to determine when the particle path is centered in the flow stream.

FIG. 9 is a schematic diagram showing two linear arrays of light sources, each positioned along an axis that is angularly offset by about ninety degrees relative to the central axis of flow of a flow channel. Each array of light sources has an annular zoned detector positioned on the opposite side of the flow stream. More specifically, a first flow sensor 300 has an array of light sources 22 (indicated as "+" signs) and an annular shaped detector 210 having a center ring 212 and outer rings 214a–d. A second flow sensor 302, which is located either upstream or downstream of the first flow sensor 300, includes an array of light sources 322 (indicated as "+" signs) and an annular shaped detector 310. In the illustrative embodiment, the annular shaped detector 310 of the second flow sensor 302 only has a center ring or region 312.

In preferred embodiments, the first flow sensor 300 is used to measure, for example, the FALS and SALS produced by one or more particles in the flow stream 50. The first flow sensor 300 may also be used to determine the lateral alignment of the path of the particles in the core stream. The second flow sensor 302 is used in conjunction with first flow sensor 300 to measure the velocity of the particles passing through flow channel 50.

To determine the velocity of each particle, the system may measure the time required for each particle to pass between the first detector 210 and the second detector 310. For example, and with reference to FIG. 9, a particle may pass detector 210 and then detector 310. By measuring the time required for the particle to travel from detector 210 to detector 310, and by knowing the distance from detector 210 to detector 310, the controller or processor 40 can calculate the velocity of the particle in the flow stream. This would be an approximate velocity measurement. This is often referred to as a time-of-flight measurement. Once the velocity is known, the time of travel through the light beam of the first or second flow sensors 300 or 310 (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the particle size, it is contemplated that laser beams may be focused both along the particle path and across the particle path. Additionally, multiple samples across the particle may be analyzed for texture features, to correlate morphological features to other particle types. This may provide multiple parameters about particle size that may help separate particle types from one another.

Figure 10:
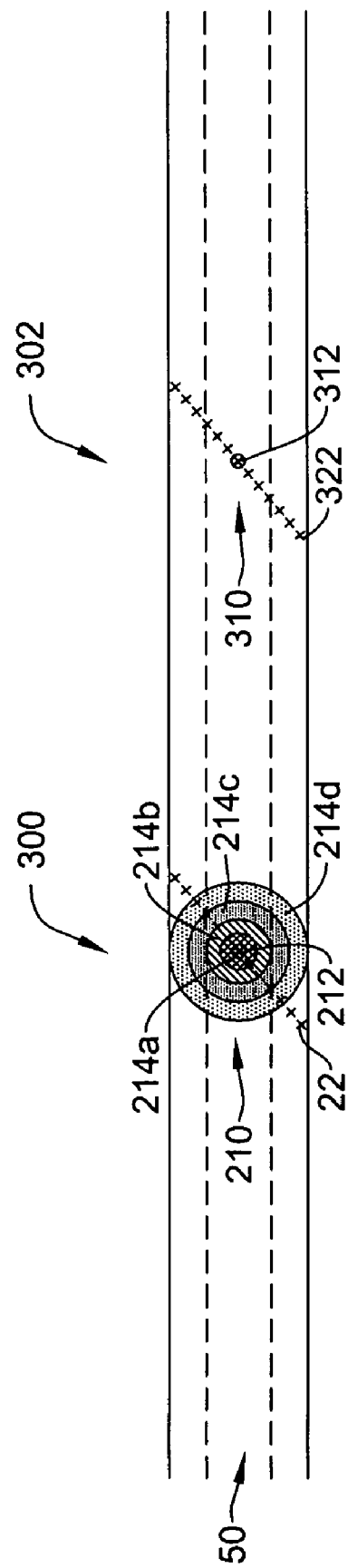
FIG. 10 is a schematic diagram showing two separate arrays of light sources, each positioned along an axis that is angularly offset by less than ninety degrees relative to the central axis of the flow stream, with two annular zoned detectors.

FIG. 10 is a schematic diagram showing two linear arrays of light sources along an axis that is angularly offset by less than ninety degrees relative to the central axis of the flow channel 50. This embodiment is similar to that shown in FIG. 9, but each of the flow sensors 300 and 302 are rotated relative to the central axis of the flow channel. One advantage of this embodiment is that the effective spacing of the light sources, as viewed by a particle, may be less than that provided by the embodiment of FIG. 9. This may allow a more uniform illumination intensity across the flow channel.

Figure 11:
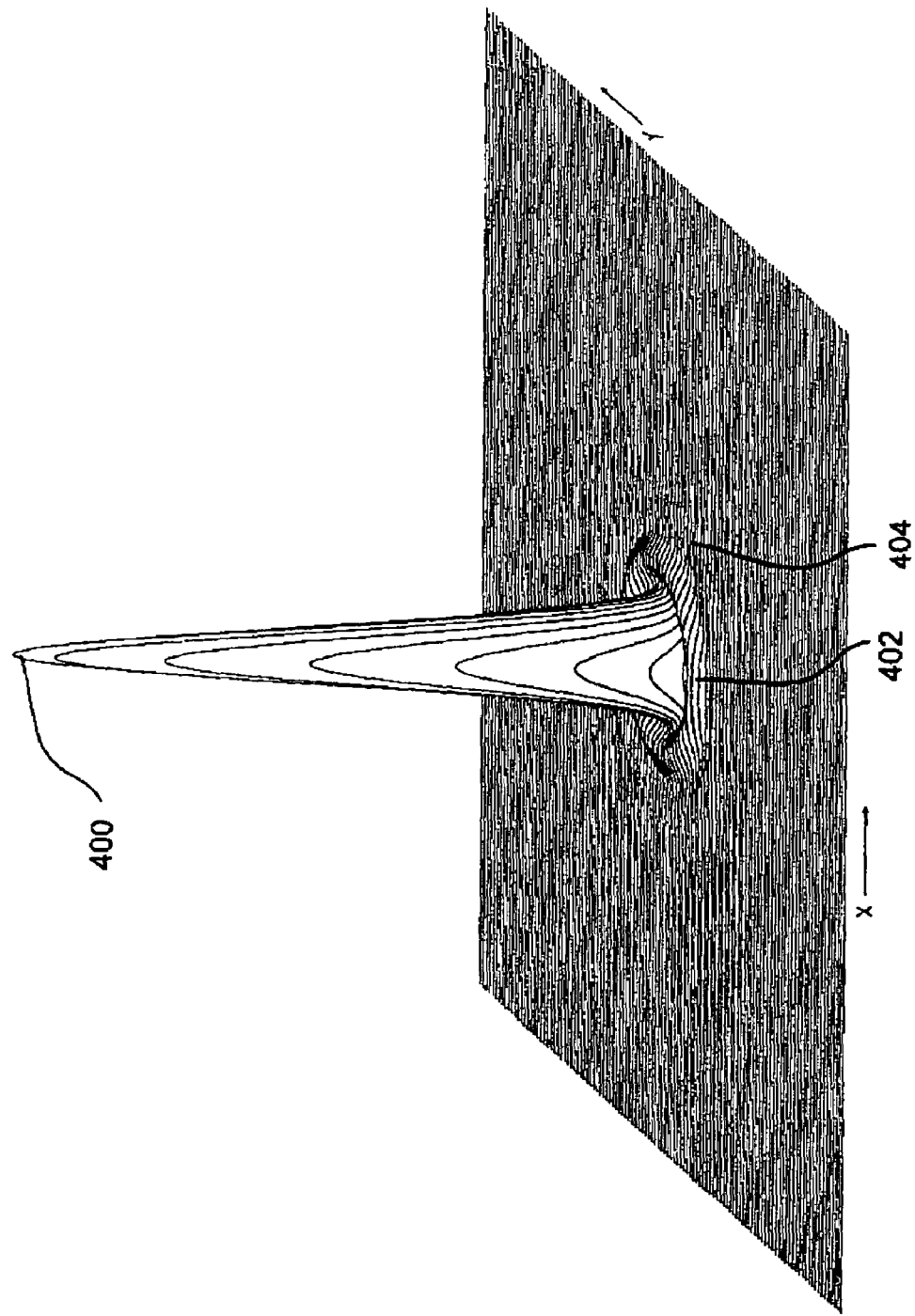
FIG. 11 is an illustrative graph representing the intensity distribution of light striking an annular detector when no particle is present in the flow channel.

FIG. 11 is an illustrative graph representing the intensity distribution of light striking the annular detector 210 of FIG. 6 with no particle in the flow channel 50. This graph shows a classic airy diffraction intensity distribution. Most of the diffraction pattern intensity is concentrated in a central zone, as shown by the center peak 400. A first outer peak 402 and a second outer peak 404 can also be observed from the graph. The first and second outer peaks 402, 404 are of substantially lesser magnitude than the first peak 400, but are large enough to be noted on the graph.

Figure 12:
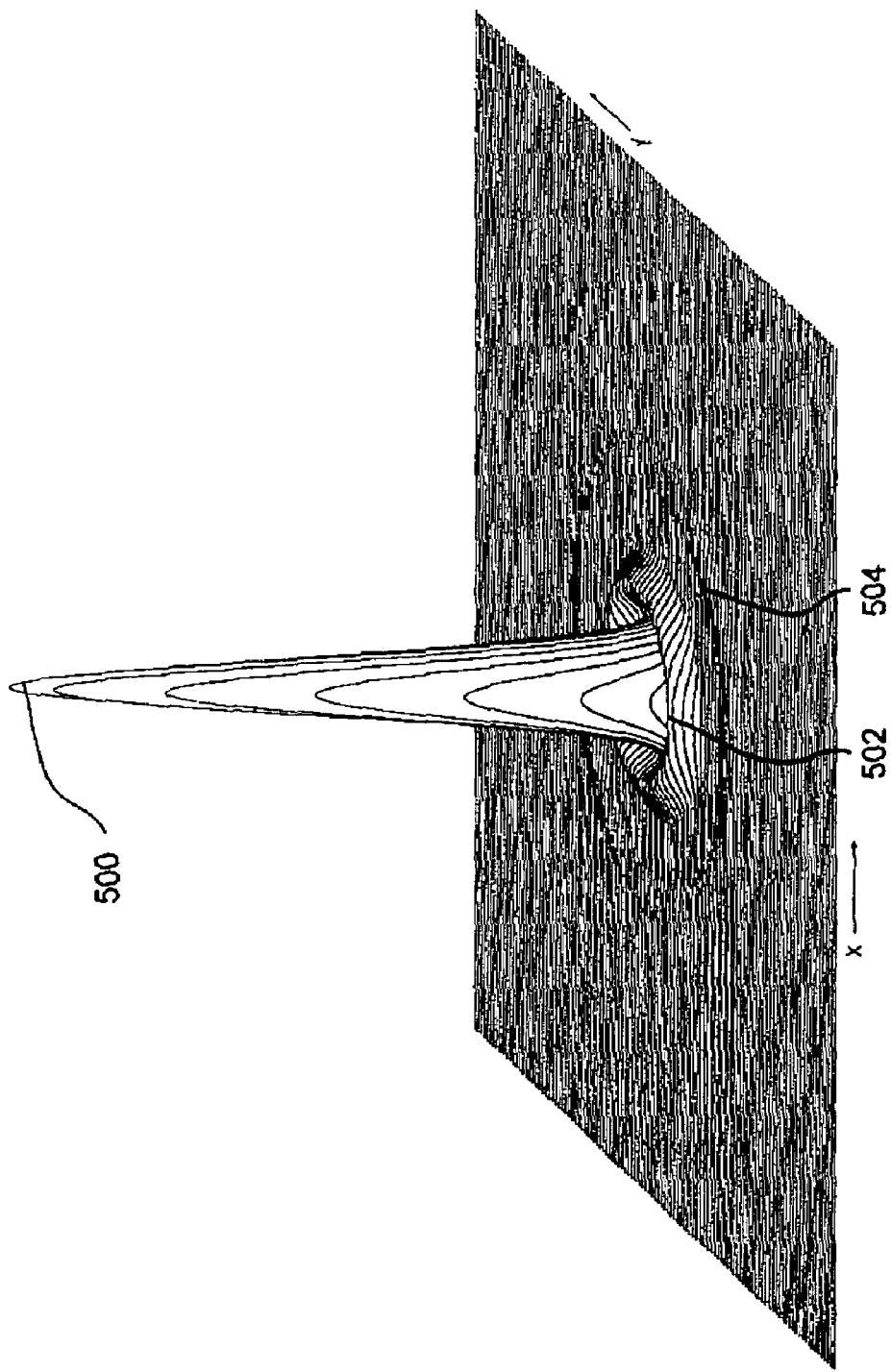
FIG. 12 is an illustrative graph representing the intensity distribution of light striking the annular detector when a particle is present in the flow channel.

FIG. 12 is an illustrative graph representing the intensity distribution of light striking the annular detector 210 of FIG. 6 when a particle is present in the flow channel 50. A central peak 500, a first outer peak 502, and a second outer peak 504 are shown. This graph demonstrates that, while the central peak 500 is similar in magnitude to the central peak 400 shown in FIG. 11, the comparative difference between the central peak 500 and the first outer peak 502 is of different magnitude than the comparative difference between central peak 400 in FIG. 11 and first outer peak 402 of FIG. 11. FIG. 12 also demonstrates that the second outer peak 504 is relatively farther away from the central peak 500 than the second outer peak 404 is from the center peak 400 of FIG. 11. These graphs also demonstrate the rotational symmetry of the light scatter signature that occurs in the present invention.

The graphs in FIGS. 11 and 12 represent data that, in preferred embodiments, is collected by the annular detector 210 of FIG. 6. This data is then sent to a processor 40 (FIG. 2) to perform various data processing functions. Possible functions include, but are not limited to, flow alignment, blood cell counting, identification of foreign objects, blood cell identification, flow speed, and identification of neutrophils and/or lymphocytes white blood cells. In a preferred embodiment, the ratio of annular zone signal strengths that are detected by the various zones in the detector 210 can be used to determine whether a blood cell is present and/or the type of blood cell present.

Figure 13:
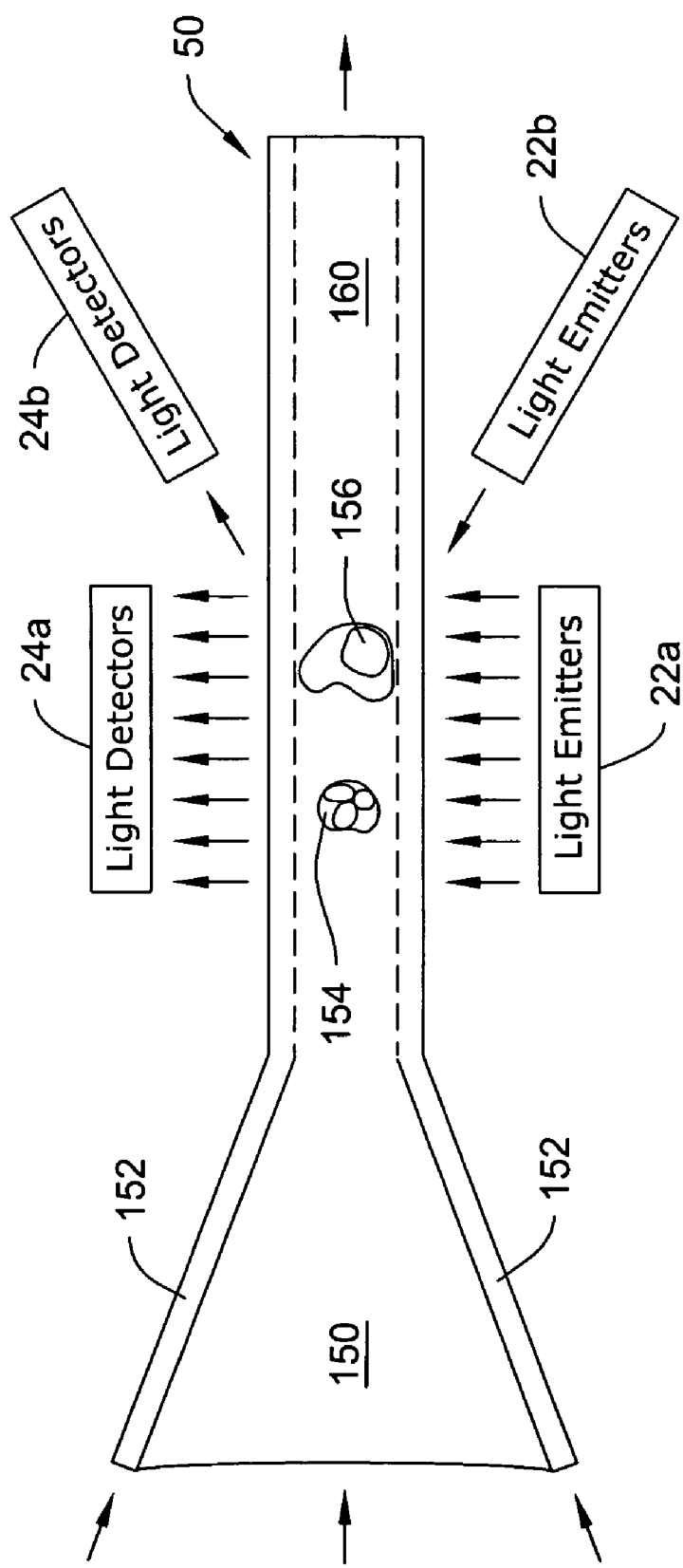
FIG. 13 is a schematic diagram showing the formation of a flow stream by the hydrodynamic focusing block 88 of FIG. 3.

FIG. 13 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. The lysing solution may have a pH lower than that of the red blood cells. This is often referred to as red cell lysing or lyse-on-the-fly. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white lood cells 154 and 156 are in single file. The velocity of the sheath fluid may be about 9 times that of the core stream 160. However, the velocity of the sheath fluid and core stream 160 remain sufficiently low to maintain laminar flow in the flow channel.

Light emitters 22*a* and 22*b*, and associated optics may be provided adjacent one side of the flow stream 50. Light detectors 24*a* and 24*b*, and associated optics are provided on another side of the flow stream 50 for receiving the light from the light emitters 22*a* and light from fluorescing particles via the flow stream 50. The output signals from the light detectors 24*a* and 24*b* are provided to controller or processor 40, wherein they are analyzed to identify and/or count selected white blood cells in the core stream 160. Light emitters 22*a* and 22*b* may be portions of light emitters 22. Likewise, light detectors 24*a* and 24*b* may be portions of light detectors 24.

Figure 14:
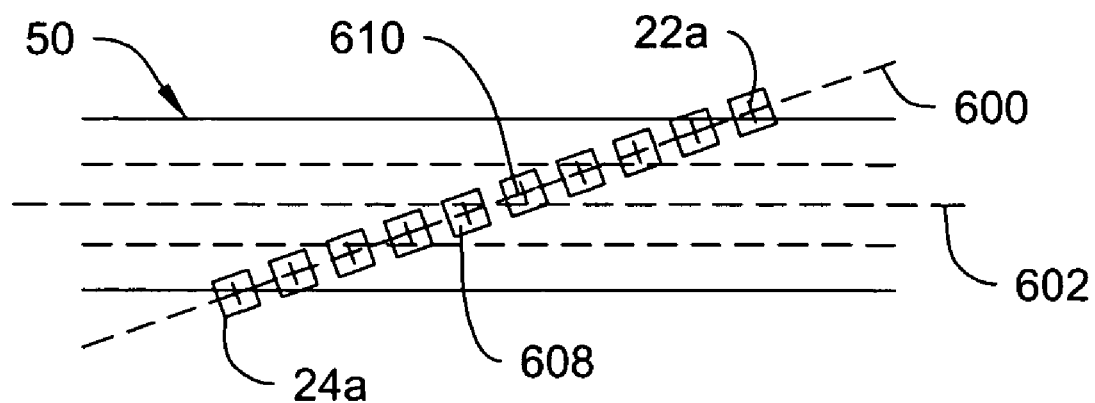
FIG. 14 is a schematic diagram showing an array of light sources and an array of light detectors for analysis of the core stream 160 of FIG. 13.

FIG. 14 is a schematic diagram showing an array 22*a* of light sources and an array 24*b* of light detectors for analysis of the core stream 160 via scattering of FIG. 13. The light sources are shown as "+" signs and the detectors are shown at boxes. In the example shown, the array of light sources is provided adjacent one side of the flow stream 50, and the array of light detectors is provided adjacent the opposite side of the flow stream. Each of the light detectors may be aligned with a corresponding one of the light sources. The array of light sources and the array of light detectors are shown arranged along a light source axis 600 that may be slightly rotated relative to the axis 602 of the flow stream 50.

The array 22*a* of light sources may be an array of lasers such as vertical cavity surface emitting lasers (VCSELs) fabricated on a common substrate. Because of their vertical emission, VCSELs are ideally suited for packaging in compact instruments such as a miniaturized portable cytometer. Such cytometer may be wearable on a person's body. The VCSELs may be "red" VCSELs that operate at wavelengths that are less than the conventional 850 nm, and such as in the 670 nm to 780 nm range. Red VCSELs may have a wavelength, power and polarization characteristic which may be ideally suited for scatter measurements.

Some prior art cytometer bench models use a single 9 mW edge-emitting laser with a wavelength of 650 nm. The beam is focussed to a 10×100 micron elongated shape to cover the uncertainty in particle position due to misalignment and width of the core stream. In contrast, the output power of the red VCSELs of the present invention, operating at 670 nm, is typically around 1 mW for a 10×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 602 offers a number of important advantages over the single light source configuration of the related art. For example, a linear array of lasers may be used to determining the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focussed spots produced by the linear array of VCSELs. The cells produce a drop in signal in the corresponding in-line reference detectors. The relative strengths of the signals may be used by the controller or processor 40 to determine the center of the particle path and a measure of the particle width.

Figure 15:
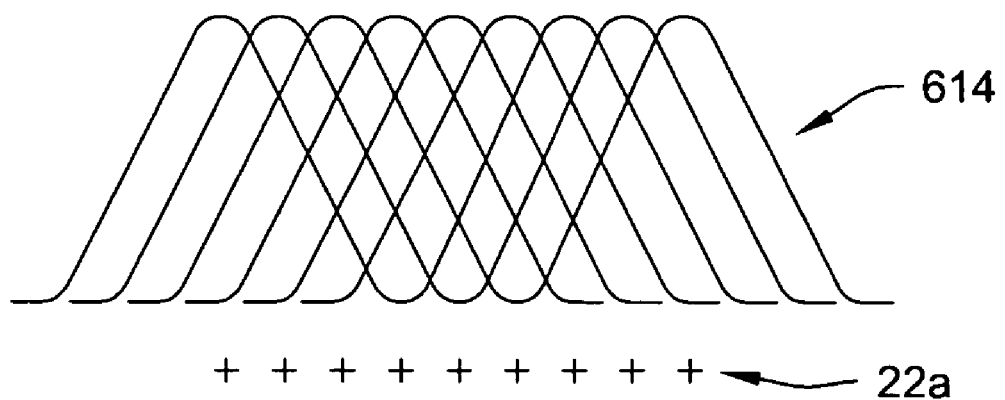
FIG. 15 is a graph showing the light intensity produced along the light source axis of FIG. 14.

For determining particle path and size, the lasers 22*a* may be focussed to a series of Gaussian spots 614 (intensity on the order of 1000 W/cm$^2$) in the plane of the core flow. The spots 614 may be about the same size as a white blood cell (10–12 um). Illustrative Gaussian spots 614 are shown in FIG. 15. Arrays 24*a* of detectors and their focussing optics are provided on the opposite side of the fluid stream 50. Lenses with fairly large F-numbers may be used to provide a working space of several hundred microns for the cytometer section of the removable cartridge.

Another advantage of using a linear array 22*a* of lasers rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 14, a cell may pass detector 608 and then detector 610. By measuring the time required for the cell to travel from detector 608 to detector 610, and by knowing the distance from detector 608 to detector 610, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22*a* of lasers rather than a single layer configuration is that a relatively or substantially constant light illumination or intensity may be provided across the flow channel or flow stream 50, particularly across the width of the flow channel or stream. This is accomplished by overlapping the Gaussian beams 614 from adjacent VCSELs 22*a*, as shown in FIG. 15. In single laser systems, or other multiple light systems, the light illumination across the flow channel may vary significantly across the channel. Thus, in such systems, if a particle is not in the center of the flow channel, the accuracy of subsequent measurements may be diminished.

Figure 16:
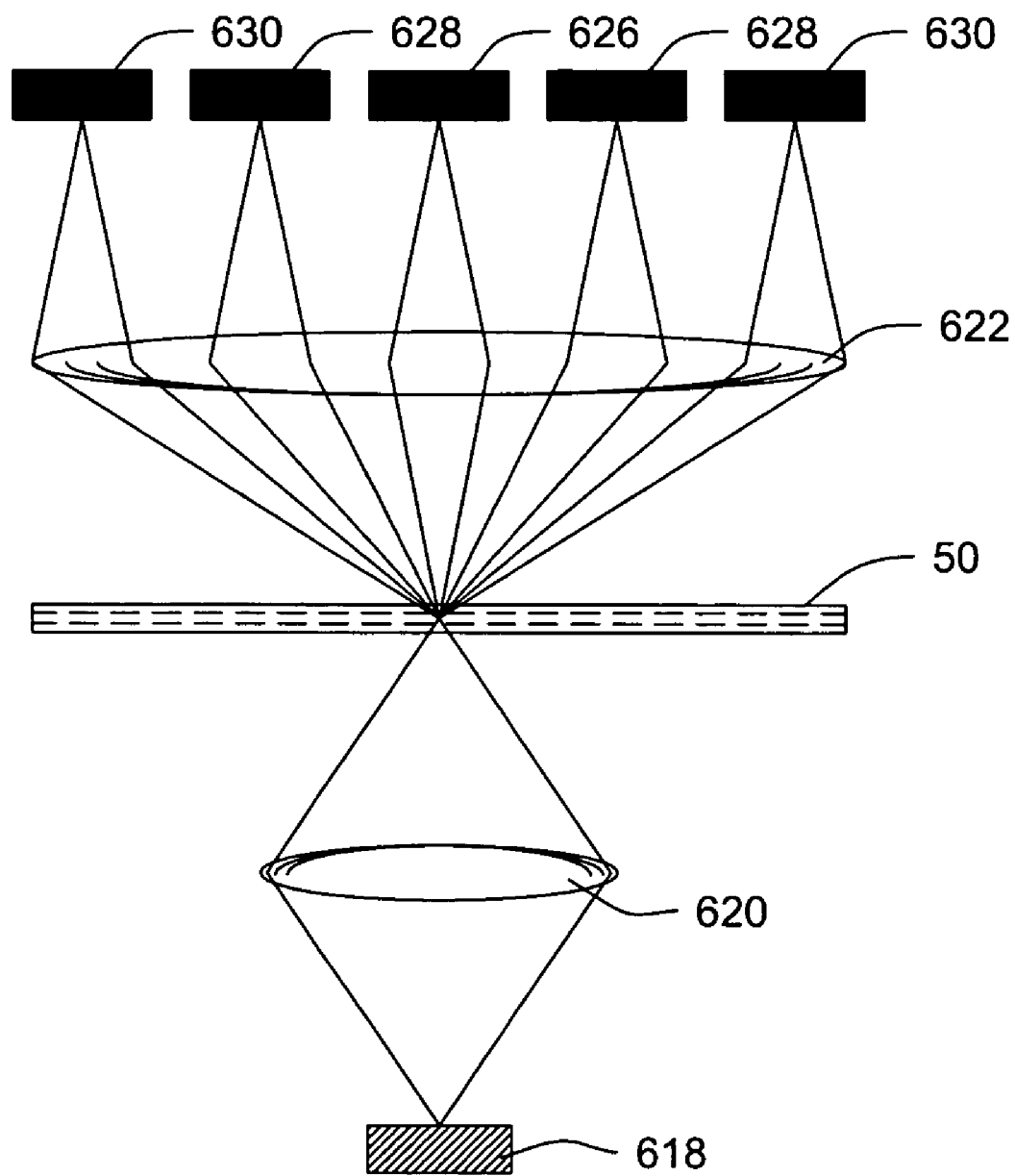
FIG. 16 is a schematic diagram showing an illustrative light source and detector pair of FIG. 14.

To perform the above described measurements, each detector 24*a* in FIG. 14 may be a single in-line detector. To measure FALS and SALS scatter, however, each detector 24*a* may further include two annular detectors disposed around the in-line detector, as shown in FIG. 16. Referring to FIG. 16, a VCSEL 618 is shown providing light in an upward direction. The light is provided through a lens 620, which focuses the light to a Gaussian spot in the plane of the core flow. Lens 620 may be a microlens or the like, which is either separate from or integrated with the VCSEL 618. The light passes through the core flow, and is received by another lens 622, such as a diffractive optical element. Lens 622 provides the light to in-line detector 626 and annular detectors 628 and 630. The in-line detector 626 may detect the light that is not significantly scattered by the particles in the core stream. Annular detector 628 may detect the forward scatter (FALS) light, and annular detector 630 may detect the small angle scatter (SALS) light.

Figure 17:
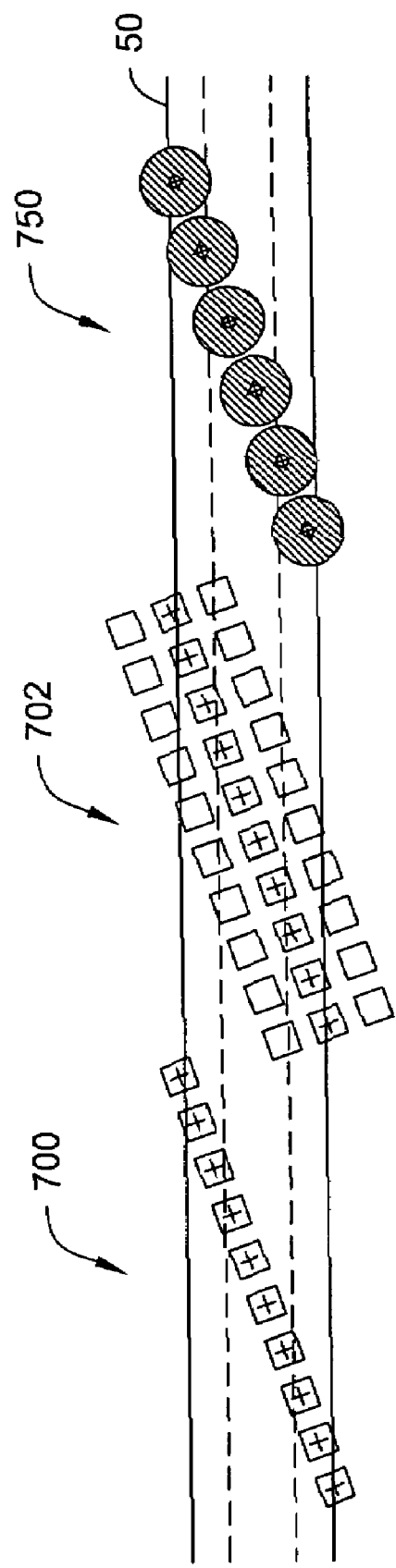
FIG. 17 is a schematic diagram showing three separate arrays of light sources and detectors, each positioned along a different light source axis that may be slightly rotated relative to the central flow axis of the flow stream of FIG. 13.

FIG. 17 shows another illustrative example of the present invention that includes three separate arrays of light sources and light detectors. Each array of light sources and light detectors are positioned along a different light source axis that may be slightly rotated relative to the central flow axis of the flow stream. By using three arrays, the optics associated with each array may be optimized for a particular application or function. For detecting small angle scattering (SALS), laser light that is well-focussed on the plane of the core flow is desirable. For detecting forward scattering (FALS), collimated light is desirable.

Referring specifically to FIG. 17, a first array of light sources and light detectors is shown at 700. The light sources and light detectors are arranged in a linear array along a first light source axis. The first light source axis may be rotated relative to the flow axis of the flow stream. The light sources and light detectors may be similar to that described above with respect to FIG. 14, and may be used to measure, for example, the lateral alignment of the cells in the flow stream, the particle size, and the velocity of the particles. It is contemplated that the in-line detectors of the third array 750 may also be used in conjunction with the in-line detectors if the first array 700 and/or second array 702 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, the optics associated with each array can be optimized for the desired application. The optics associated with the first array 700 may be designed to provide well-focussed laser light on the plane of the core flow. This helps provide resolution to the alignment, size and particle velocity measurements performed by the first array 700. Likewise, the optics associated with the second array 702 may be designed to provide well-focussed laser light on the plane of the core flow. Well focussed light is desirable when measuring the small angle scattering (SALS) produced by selected particles in the flow stream. Finally, the optics associated with the third array 750 may be designed to provide collimated light to the core flow. As indicated above, collimated light is desirable when measuring forward angle scattering (FALS) produced by selected particles in the flow stream.

Having thus described the preferred embodiments of the present invention, those of skill in the art will readily appreciate that the teachings found herein may be applied to yet other embodiments within the scope of the claims hereto attached.

What is claimed is:

1. A method for determining the scattering produced by one or more particles in a stream in a flow channel, the method comprising:
   activating a linear array of light sources to provide a substantially constant light intensity across a width of the flow channel;
   receiving with a light detector the substantially constant light intensity provided across the width of the flow channel by the linear array of light sources; and
   wherein the substantially constant light intensity provided across the width of the flow channel provides for consistent measurement accuracy across the width of the flow channel.

2. The method of claim 1, wherein the linear array of light sources is non-parallel to the flow channel.

3. The method of claim 1, further comprising analyzing a scatter pattern produced by the one or more particles in a stream in the flow channel as detected by the light detector.

4. The method of claim 3, further comprising:
   activating a second linear array of light sources to provide a second substantially constant light intensity across the width of the flow channel; and
   receiving with a second light detector the second substantially constant light intensity provided across the width of the flow channel by the second linear array of light sources.

5. The method of claim 4, wherein the second linear array of light sources is non-parallel to the flow channel.

6. The method of claim 4, further comprising determining a velocity of one or more particles in the stream in the flow channel from the light detectors.

7. An apparatus for analyzing one or more particles in a stream in a flow channel, the apparatus comprising:
   a linear array of light sources for providing a substantially constant light intensity across a width of the flow channel; and
   a light detector for receiving the substantially constant light intensity across the width of the flow channel from the linear array of light sources.

8. The apparatus of claim 7, wherein the linear array of light sources is non-parallel to the flow channel.

9. The apparatus of claim 7, further comprising a processor, connected to the light detector, for analyzing a scatter pattern produced by one or more particles in a stream in the flow channel as detected by the light detector.

10. The apparatus of claim 9, further comprising:
    a second linear array of light sources for providing a second substantially constant light intensity across the width of the flow channel; and
    a second light detector for receiving the substantially constant light intensity across the width of the flow channel from the second linear array of light sources.

11. The apparatus of claim 10, wherein the second linear array of light sources is non-parallel to the flow channel.

12. The apparatus of claim 10, wherein the processor is connected to the second light detector for determining a velocity of one or more particles in the stream in the flow channel.

* * * * *